United States Patent [19]

Touda et al.

[11] Patent Number: 4,462,890
[45] Date of Patent: Jul. 31, 1984

[54] OXYGEN SENSING ELEMENT HAVING BARRIER LAYER BETWEEN CERAMIC SUBSTRATE AND SOLID ELECTROLYTE LAYER

[75] Inventors: Masayuki Touda; Yoshio Akimune; Kazuo Matoba, all of Yokosuka, Japan

[73] Assignee: Nissan Motor Company, Limited, Yokohama, Japan

[21] Appl. No.: 348,835

[22] Filed: Feb. 16, 1982

[30] Foreign Application Priority Data

Feb. 20, 1981 [JP] Japan .................................. 56-22962

[51] Int. Cl.$^3$ ............................................. G01N 27/58
[52] U.S. Cl. ..................................... 204/425; 204/426
[58] Field of Search .................... 204/195 S, 1 S, 425, 204/426; 338/34; 422/94

[56] References Cited

U.S. PATENT DOCUMENTS

| | | | |
|---|---|---|---|
| 4,040,929 | 8/1977 | Bauer et al. ..................... | 204/195 S |
| 4,298,573 | 11/1981 | Fujishiro ............................... | 422/94 |
| 4,300,991 | 11/1981 | Chiba et al. ..................... | 204/195 S |
| 4,306,957 | 12/1981 | Ishitani et al. .................. | 204/426 X |

FOREIGN PATENT DOCUMENTS

| | | | |
|---|---|---|---|
| 0012647 | 6/1980 | European Pat. Off. ......... | 204/195 S |
| 2304464 | 8/1974 | Fed. Rep. of Germany ... | 204/195 S |
| 2718907 | 11/1978 | Fed. Rep. of Germany ... | 204/195 S |
| 2428838 | 1/1980 | France ............................. | 204/195 S |
| 2451031 | 10/1980 | France ............................. | 204/195 S |

*Primary Examiner*—G. L. Kaplan
*Attorney, Agent, or Firm*—Schwartz, Jeffery, Schwaab, Mack, Blumenthal & Koch

[57] ABSTRACT

An oxygen sensing element having a ceramic substrate, a layer of an oxygen ion conductive solid electrolyte such as zirconia containing a stabilizing oxide such as yttria, and a pair of electrode layers formed on one side of the solid electrolyte layer so as to be spaced from each other. To prevent a significant change in the output characteristic of the element caused by diffusion of the stabilizing oxide from the solid electrolyte layer into the ceramic substrate, there is a barrier layer which intervenes between the substrate and the solid electrolyte layer at least in a region between the two electrode layers. The barrier layer is formed of a ceramic material such as the above mentioned solid electrolyte or a metal such as platinum, or has a double-layer structure consisting of a metal layer in direct contact with the substrate and an outer layer formed of a ceramic material.

6 Claims, 11 Drawing Figures

OXYGEN SENSING ELEMENT HAVING BARRIER LAYER BETWEEN CERAMIC SUBSTRATE AND SOLID ELECTROLYTE LAYER

BACKGROUND OF THE INVENTION

The present invention relates to an oxygen sensing element of the type having an oxygen ion conductive solid electrolyte layer supported on a ceramic substrate and a pair of electrode layers formed adjacent the solid electrolyte layer.

Oxygen sensors utilizing an oxygen ion conductive solid electrolyte such as zirconia stabilized with calcia or yttria are widely used for detection of concentrations of oxygen in various gas atmospheres. Particularly in the automotive industry it has become common to install such an oxygen sensor in the exhaust system as a means for detecting actual air/fuel ratio values in the engine. In this the automotive field, a recent trend is to miniaturize the oxygen sensitive element of the sensor by constructing it as a laminate of thin, film-like layers on a ceramic substrate of very small size. The principal part of the laminate is a combination of solid electrolyte layer and a pair of electrode layers, which constitutes a sort of oxygen concentration cell. Usually an electric heater is embedded in the substrate to maintain the oxygen sensing element in operation at a sufficiently elevated temperature such as 600°–800° C. because the solid electrolyte oxygen concentration cell does not properly function at temperatures below a certain level such as about 400° C.

In many cases the two electrode layers in an oxygen sensing element of the laminate type are formed on the two opposite sides of the solid electrolyte layer so that one of the electrode layers is closely sandwiched between the ceramic substrate and the solid electrolyte layer. However, it is also possible to construct an oxygen sensing element that operates on the same principle by forming both of the two electrode layers on the same side of the solid electrolyte layer with a narrow gap between the two electrode layers. In this case, the solid electrolyte layer makes direct contact with the surface of the ceramic substrate at least in a portion existing between the two electrode layers.

In producing a solid electrolyte oxygen sensing element the content of the stabilizing oxide such as yttria in the solid electrolyte such as zirconia is carefully controlled to thereby control the proportion of cubic zirconia to monoclinic zirconia in the resultant solid electrolyte and to afford the solid electrolyte with optimal electric characteristics. However, when the solid electrolyte layer in the oxygen sensing element is in direct contact with the substrate of a ceramic material such as alumina, there occurs a considerable change in the content of the stabilizing oxide in the solid electrolyte layer during sintering of the solid electrolyte in the production of the oxygen sensing element and also during long use of the oxygen sensing element in a heated state. The reason is presumed to be diffusion of the stabilizing oxide from the solid electrolyte layer into the ceramic substrate. Such a change in the content of the stabilizing oxide in the solid electrolyte layer is accompanied by changes is the resistance and polarizing characteristic of the solid electrolyte layer and, hence, results in a considerable change in the output characteristic of the oxygen sensing element.

SUMMARY OF THE INVENTION

It is an object of the present invention to provide an oxygen sensing element of the type having a layer of an oxygen ion conductive solid electrolyte containing a stabilizing oxide supported on a ceramic sbstrate and a pair of electrode layers both of which are formed on one side of the solid electrolyte layer, which does not suffer from diffusion of the stabilizing oxide from the solid electrolyte existing between the two electrode layers into the substrate and, hence, will remain unchanged over long periods in its output characteristic in practical operations.

An oxygen sensing element according to the invention comprises a substrate made of a ceramic material, a barrier layer formed on a major surface of the substrate, a microscopically porous layer of an oxygen ion conductive solid electrolyte containing a stabilizing oxide formed on the barrier layer, and microscopically porous first and second electrode layers which are formed on one side of the solid electrolyte layer so as to be spaced from each other. The barrier layer, the solid electrolyte layer and the two electrode layers are arranged such that the barrier layer intervenes between the substrate and the solid electrolyte at least in a region between the first and second electrode layers, and the barrier layer is formed of an inorganic heat-resistant material through which the stabilizing oxide hardly diffuses.

It is preferred to use the solid electrolyte containing the above-mentioned stabilizing oxide mentioned as the material of the barrier layer as well. When the oxygen sensing element is designed such that the two electrode layers do not make contact with the barrier layer, it is preferred to use a metal, particularly platinum, as the material of the barrier layer. When the two electrode layers are in direct contact with the barrier layer, it is preferred that the barrier layer has a double-layer structure consisting of a platinum layer laid directly on the major surface of the substrate and a solid electrolyte layer which is laid on the platinum layer so as to make close contact with the two electrode layers and the solid electrolyte existing between the two electrode layers.

To detect the concentration of oxygen in a gas atmosphere by using an oxygen sensing element according to the invention, the element is disposed in the gas atmosphere so that both of the two electrode layers are exposed to the gas atmosphere either directly or through the microscopically porous solid electrolyte layer. During operation, a constant DC current of an adequate intensity, such as tens of microamperes, is supplied to the sensitive part of the element so as to flow from the first electrode layer to the second electrode layer through the solid electrolyte between the two electrode layers. A joint effect of electrode reactions at the respective electrode layers, is the migration of oxygen ions through the solid electrolyte from the second electrode layer to the first electrode layer and the diffusion of oxygen molecules through the micropores in the solid electrolyte layer. This produces a difference between the partial pressure of oxygen at the first electrode layer and that at the second electrode layer. Then the solid electrolyte existing between the two electrode layers acts as an oxygen concentration cell, and therefore a potential difference is produced between the two electrode layers. The magnitude of this potential difference depends on the partial pressure or concentration of oxygen in the gas atmosphere in which the oxygen sensing element is disposed. Usually this oxygen sensing element has an electric heater element which is embedded in the substrate and kept energized so as to keep the element in operation at a suitably elevated temperature.

An oxygen sensing element according to the invention can be produced in very small size by using a so-called thick-film technique and will remain unchanged over a long period in its output characteristic, i.e. the relationship between the concentration of oxygen in a gas subject to measurement and the aforementioned potential difference, even though the element is continuously operated in a heated state, because the barrier layer effectively suppresses the diffusion of the stabilizing oxide from the solid electrolyte existing between the two electrode layers into the ceramic substrate. The barrier layer is also effective for preventing changes in the chemical and electrical properties of the solid electrolyte layer as the principal component of the element during sintering of the solid electrolyte layer in the production of the element.

DESCRIPTION OF THE PREFERRED EMBODIMENTS

Figure 1:
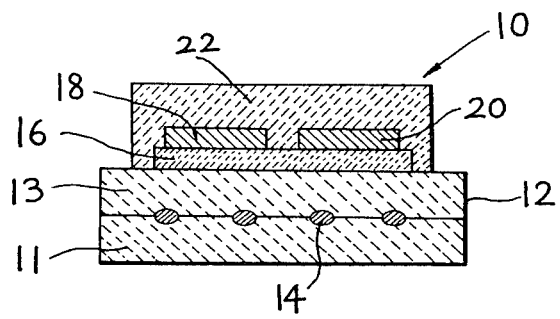
FIG. 1 is a sectional and explanatory view of an oxygen sensing element as an embodiment of the present invention.
Figure 2:
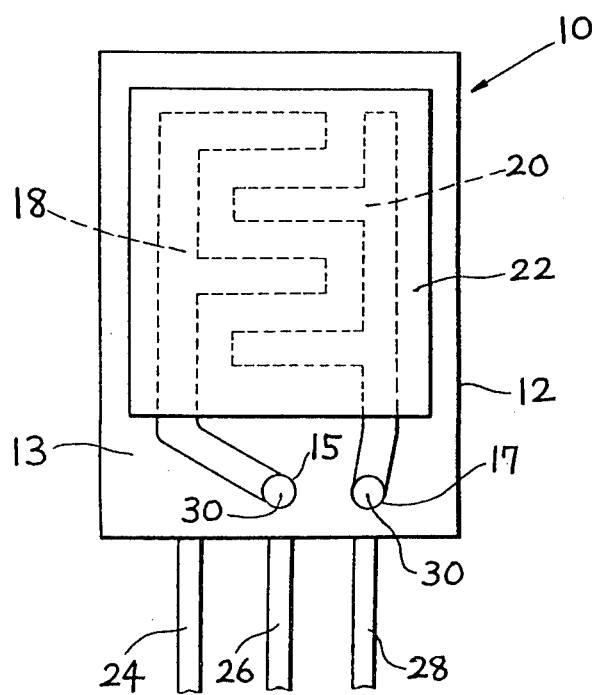
FIG. 2 is a plan view of the oxygen sensing element of FIG. 1.

FIGS. 1 and 2 show an oxygen sensing element 10 embodying the present invention. A structurally basic member of this element 10 is a base plate or substrate 12 which is made of an electrochemically inactive ceramic material such as alumina, forsterite, steatite, mullite or spinel. A heater element 14 in the form of either a thin wire or a thin layer of an electrically resistive metal is embedded in the substrate 12. In practice, the substrate 12 is prepared by face-to-face bonding of two ceramic sheets 11 and 13 one of which is precedingly provided with the heater element 14.

The sensitive part of this oxygen sensing element 10 takes the form of a laminate of thin layers supported on the ceramic substrate 12. The laminate includes a barrier layer 16 formed on a major surface of the substrate 12 so as to cover a sufficiently large area of the substrate surface. In this embodiment, the barrier layer 16 is formed of a ceramic material. A first electrode layer 18 having a comb-like shape and a second electrode layer 20 having a comb-like shape are formed on the upper surface of the barrier layer 16 in a nearly meshed but spaced arrangement such that the opposite segments of these two electrode layers 18 and 20 are at an approximately constant distance from each other. The material of the two electrode layers 18, 20 is a metal which is high in electronic conductivity and exhibits a catalytic activity on oxidation reactions of carbon monoxide and hydrocarbons, or a conductive cermet containing such a metal. Platinum and platinum alloys are preferred examples of useful metals. These two electrode layers 18 and 20 must be so formed as to have a microscopically porous and gas-permeable structure. As the outermost layer of the aforementioned laminate, there is a layer 22 of an oxygen ion conductive solid electrolyte, such as $ZrO_2$ or $Bi_2O_3$ containing a small amount of a stabilizing oxide such as $Y_2O_3$, CaO or MgO. This solid electrolyte layer 22 covers the two electrode layers 18 and 20 entirely except their terminal portions and fills the gap between the two electrode layers 18 and 20 so as to make close contact with the barrier layer 16. In a peripheral region, the solid electrolyte layer 22 covers a peripheral region of the barrier layer 16 and makes close contact with the upper surface of the substrate 12. The solid electrolyte layer 22 must be so formed as to have a microscopically porous and gas-permeable structure.

Each layer of the above described laminate can be formed by applying a paste containing a powdered material for the barrier, electrode or solid electrolyte layer onto the surface of the substrate of the underlying layer(s) by screen-printing for instance and subsequently sintering the powdered material contained in the applied paste. Alternatively, each layer may be formed by a physical vapor deposition method such as sputtering or vacuum evaporation, or by flame or plasma spraying.

The oxygen sensing element 10 has three lead wires 24, 26 and 28 which are inserted into the substrate 12 in their tip portions. The first lead wire 24 is connected to one terminal of the heater 14 within the substrate 12. The second lead wire 26 is connected to the first electrode layer 18 by using a hole 15 formed in the upper half 13 of the substrate 12 and a conductor 30 filled in the hole 15. A terminal portion of the first electrode layer 18 extends to this hole 15, and the inserted tip portion of the lead wire 26 reaches right beneath the hole 15. Similarly, the third lead wire 28 is connected to the second electrode layer 20 by using a hole 17 formed in the upper half 13 of the substrate 12 and conductor 30 filled in this hole 17. Furthermore, this lead wire 28 is connected to the other terminal of the heater 14 within the substrate 12.

FIGS. 3(A) to 3(D) illustrate a preferred process of producing the oxygen sensing element 10 of FIGS. 1 and 2.

Figure 3A:
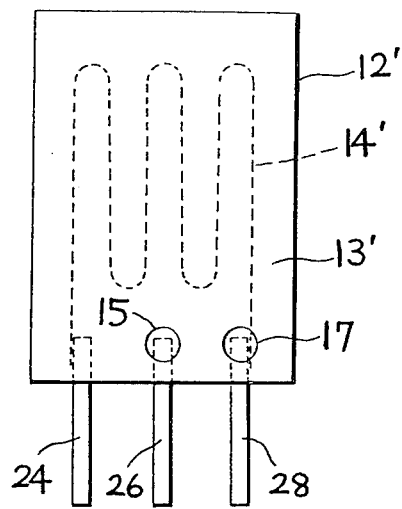
FIGS. 3(A) and 3(D) illustrate an exemplary process of producing the oxygen sensing element of FIGS. 1 and 2.

FIG. 3(A) shows an intermediate 12' of the ceramic substrate 12 prepared in the following way. First, a paste containing 70% by weight of a platinum powder dispersed in an organic liquid vehicle is applied onto a major surface of a rectangular sheet (unseen) of green or unfired alumina by utilizing the technique of screen-printing so as to form a paste layer 14' in the pattern of an elongate and meandering or zigzag path. For example, the green alumina sheet is 5 mm × 10 mm wide and 0.7 mm thick. After drying of the printed paste layer 14', tip portions of the three lead wires 24, 26 and 28 (for example, platinum wires each 0.2 mm in diameter and 7 mm in length) are placed on the green alumina sheet in a parallel and spaced arrangement. The tip portions of the first and third lead wires 24 and 28 lie on the terminal regions of the platinum paste layer 14', respectively, while the tip portion of the second lead wire 26 lies in the middle between the other lead wires 24 and 28 without making contact with any region of the paste layer 14'. Then another green alumina sheet 13' is placed on the paste-applied green alumina sheet. The two sheets of green alumina are identical in material and dimensions, but the upper sheet 13' is formed with two through-holes 15 and 17 such that the tip portions of the second and third lead wires 26 and 28 are partly exposed to the atmosphere through these two holes 15 and 17, respectively. The green alumina sheet 13' is bonded to the lower green alumina sheet by heating the piled two sheets to about 100° C. and applying a pressure of about 5 kg/cm².

Figure 3B:
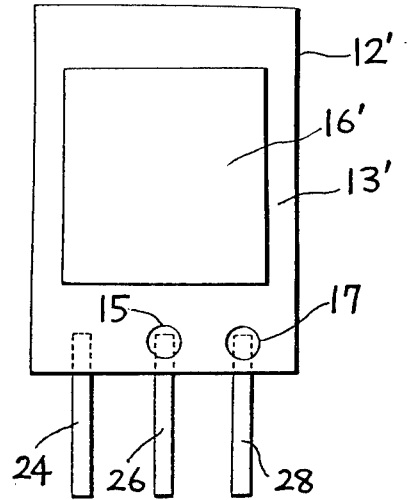

Referring to FIG. 3(B), a paste prepared by dispersing 70 parts by weight of a powdered solid electrolyte material consisting of 95 mol % of $ZrO_2$ and 5 mol % of $Y_2O_3$ in 30 parts by weight of an organic liquid vehicle is applied onto the upper surface of the unfired substrate 12' by screen-printing so as to form a paste layer 16', which has a thickness of about 10 μm after drying.

Figure 3C:
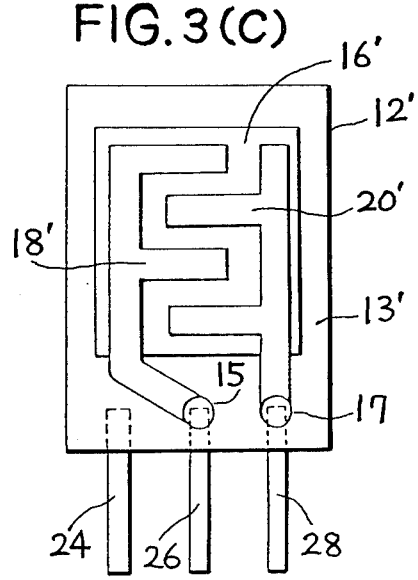

Next, as shown in FIG. 3(C), the aforementioned platinum paste is applied onto the outer surface of the dried solid electrolyte layer 16' by screen-printing so as to form two comb-shaped paste layers 18' and 20'. These two comb-shaped layers 18' and 20' are patterned so as to be at a constant and very short distance, such as 0.2 mm, from each other over an entire length of their oppositely arranged portions. A terminal portion of the first conductive paste layer 18' extends to the periphery of the hole 15, and a terminal portion of the second conductive paste layer 20' extends to the periphery of the other hole 17. For example, these conductive paste layers 18' and 20' have a uniform thickness of 15 μm after drying.

With a view to enhancing the strength of adhesion of the electrode layers 18 and 20 in the oxygen sensing element 10 to the barrier layer 16 and the solid electrolyte layer 22, it is optional for form the conductive paste layers 18' and 20' in FIG. 3(C) by using a cermet paste containing a platinum powder and a powder of a ceramic material such as alumina or zirconia instead of the platinum paste.

Figure 3D:
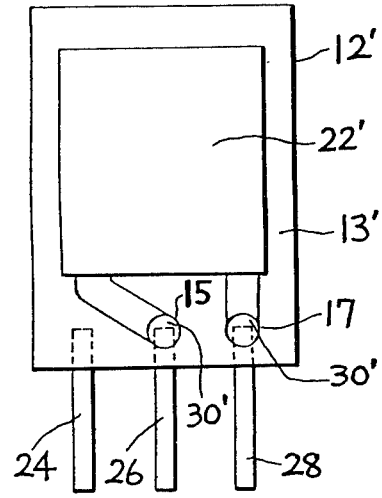

Referring to FIG. 3(D), the solid electrolyte paste mentioned with reference to FIG. 3(B) is applied onto the outer surfaces of the element in the state of FIG. 3(C) by screen-printing so as to form a solid electrolyte paste layer 22', which completely covers the comb-shaped and oppositely arranged portions of the conductive paste layers 18' and 20' and the exposed regions of the paste layer 16'. For example, the thickness of this solid electrolyte paste layer 22' after drying is about 20 μm measured from the upper surfaces of the conductive paste layers 18' and 20'. Then, the platinum paste or the conductive cermet paste used at the stage of FIG. 3(C) is filled into the two holes 15 and 17 as indicated at 30' in FIG. 3(D) in order to establish electrical connection between the second lead wire 26 and the first conductive paste layer 18' and between the third lead wire 28 and the second conductive paste layer 20'.

The unfired element in the state of FIG. 3(D) is fired in air for about 2 hr at 1480° C., for example, to simultaneously sinter the green alumina substrate 12', platinum layer 14' in the substrate 12', the laminate of dried paste layers 16', 18', 20', 22' and the dried conductive paste 30' in the holes 15 and 17. By this firing operation, the green alumina substrate 12' turns into the rigid alumina substrate 12 of the oxygen sensing element 10 and the platinum layer 14' in the green alumina substrate 12' into the heater layer 14. Simultaneously, the solid electrolyte layer 16', first platinum layer 18', second platinum layer 20' and solid electrolyte layer 22' in FIGS. 3(C) and 3(D) turn into the sintered barrier layer 16, first electrode layer 18, second electrode layer 20 and solid electrolyte layer 22, respectively, while the conductive paste 30' in the holes 15 and 17 turns into the sintered conductors 30.

To detect the concentration of oxygen in a gas atmosphere, the oxygen sensing element 10 of FIGS. 1 and 2 is used in the following manner. The element 10 is entirely disposed in the gas atmosphere subject to measurement, so that the first and second electrode layers 18 and 20 are both exposed to the gas atmosphere through the microscopically porous solid electrolyte layer 22. The heater 14 in the substrate 12 is connected to a DC power supply by using the first and third lead wires 24 and 28 such that a current flows from the first lead wire 24 to the third lead wire 28. The current is controlled so as to maintain the oxygen sensing element 10 at a constant and sufficiently elevated temperature, which is usually about 600° C. The second lead wire 26 is connected to the positive terminal of another DC power supply, and the third lead wire 28 is connected to the negative terminal of this power supply, too. This power supply is controlled such that a constant DC current of the order of $10^{-6}$ to $10^{-3}$ A continuously flows from the first electrode layer 18 toward the second electrode layer 20 through the oxygen ion conductive solid electrolyte 22 which occupies the gap between the first and second electrode layers 18 and 20. Furthermore, the second and third lead wires 26 and 28 are connected to a potentiometer or an equivalent circuit to measure a potential difference V between the first and second electrode layers 18 and 20.

The potential difference V is expressed by the following equation.

$$V = E + I_C \cdot R_S$$

wherein $I_C$ represents the current flowing from the first electrode 18 to the second electrode 20, $R_S$ represents the resistance of the solid electrolyte intervening between the two electrode layers, and E represents a potential attributed to electrode reactions at the first and second electrode layers.

In the potential difference according to this equation, the component $I_C \cdot R_S$ is constant when the solid electrolyte 22 is maintained at a constant temperature, and this component $I_C \cdot R_S$ can be made small relative to the other component E by forming the first and second electrode layers 18 and 29 at a very short distance therebetween as mentioned hereinbefore and also by so energizing the heater 14 as to maintain the oxygen sensing element 10 at a sufficiently high temperature thereby lowering the resistance $R_S$ of the solid electrolyte 22.

The magnitude of the potential E depends on the concentration or partial pressure of oxygen in the gas atmosphere in which the oxygen sensing element 10 is disposed because this potential E is produced by the following process. At the second electrode layer 20, oxygen molecules diffused from the ambient gas atmosphere through the micropores in the solid electrolyte layer 22 are ionized to form oxygen ions since the DC current $I_C$ is flowing from the first elelectrode layer 18 to the second electrode layer 20, and the formed oxygen ions migrate through the solid electrolyte 22 existing in the gap between the two electrode layers 18 and 20 toward the first electrode layer 18 as an effect of the current $I_C$ through the solid electrolyte. Upon arrival at the first electrode layer 18 the oxygen ions are converted to oxygen molecules. Although these oxygen molecules will gradually diffuse to the ambient atmosphere through the micropores in the solid electroylte layer 22, there remains a tendency for oxygen to accumulate in the vicinity of the electrode layer 18. Consequentially the partial pressure of oxygen in the vicinity of the first electrode layer 18 remains higher than the partial pressure of oxygen in the vicinity of the second electrode layer 20, and therefore that portion of the solid electrolyte 22 which intervenes between the two electrode layers 18 and 22 acts as an oxygen concentration cell. Therefore, polarization occurs between the first and second electrode layers 18 and 20 in dependence on the resistance of the micropores in the solid electrolyte layer 22 to the diffusion of oxygen molecules therethrough and the rates of the electrode reactions at the respective electrode layers 18 and 20, and the magnitude of the potential E attributed to the polarization depends on the partial pressure of oxygen in the gas atmosphere subject to measurement. As the partial pressure or concentration of oxygen in the gas atmosphere becomes lower and therefore the diffusion of oxygen molecules to the electrode layers through the solid electrolyte layer 22 decreases, the potential E becomes higher because then the effect of the transfer of oxygen in the form of ions from the second electrode layer 20 to the first electrode layer 18 becomes more significant.

An important feature of the above described oxygen sensing element 10 is the existence of the barrier layer 16 which is formed of $ZrO_2$ containing $Y_2O_3$ similarly to the overlying solid electrolyte layer 22. This barrier layer 16 intervenes between the alumina substrate 12 and the solid electrolyte 22 existing between the first and second electrode layers 18 and 20 for the purpose of suppressing the diffusion of $Y_2O_3$ from the solid electrolyte 22 existing between the two electrode layers 18 and 20 into the substrate 12 during operation of the element 10 in a heated state and also during sintering of the solid electrolyte layer 22 in producing the element 10. Owing to the use of the same yttria-containing composition for both the solid electrolyte layer 22 and the barrier layer 16, the barrier layer 16 accomplishes its purpose and consequentially prevents the solid electrolyte 22 existing between the two electrode layers 18 and 20 from undergoing a change in its electric characteristic with the lapse of time.

To carry out an experiment to confirm the effect of the barrier layer 16, some samples of the oxygen sensing element 10 were produced by the method described with reference to FIGS. 3(A) to 3(D). For comparison, some samples of a different oxygen sensing element were produced by omitting the formation of the barrier layer 16 in the above described production method and by using a powdered solid electrolyte material consisting of 92 mole % of $ZrO_2$ and 8 mole % of $Y_2O_3$ as the solid component of the paste for forming the solid electrolyte layer 22. The amount of $Y_2O_3$ in the raw material was increased in view of some diffusion of $Y_2O_3$ from the solid electroltye layer 22 under sintering into the substrate 12. After the sintering, the $Y_2O_3$ content in the solid electrolyte layer 22 of each sample was measured by X-ray diffraction analysis, and only the samples containing 5 mole % of $Y_2O_3$ in the solid elecrolyte layer 22 were used in the experiment.

Figure 4:
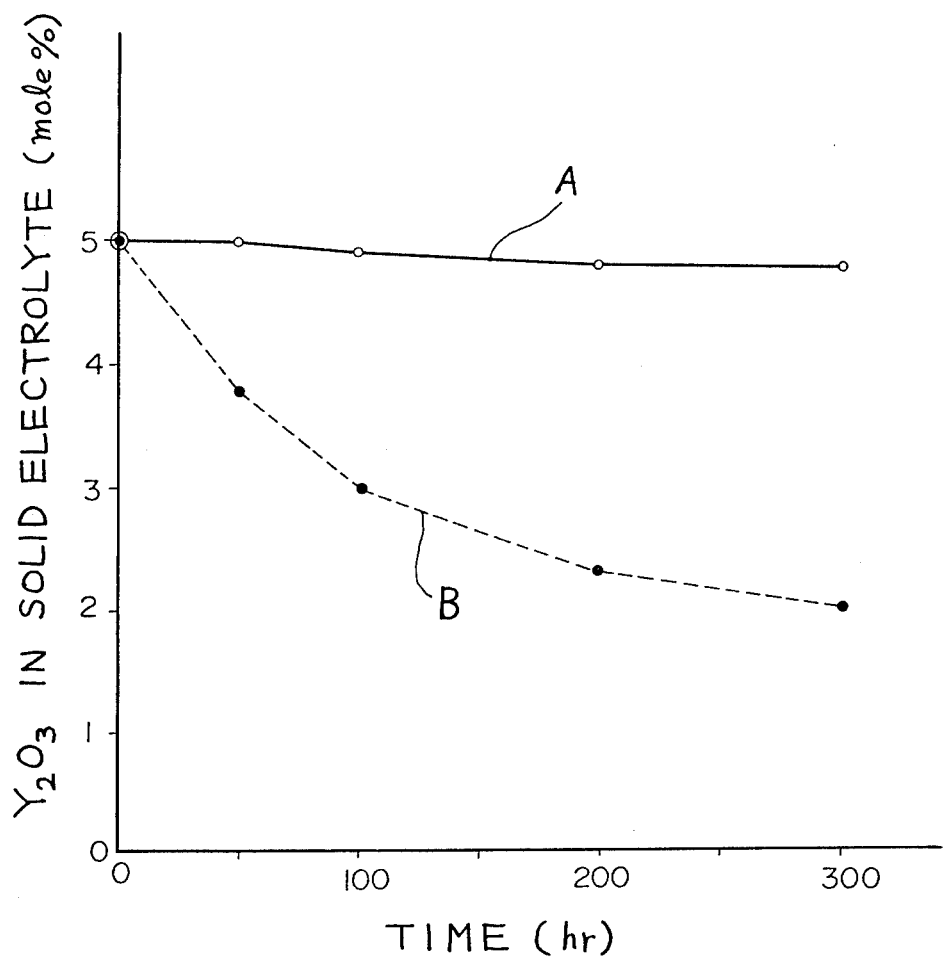
FIG. 4 is a graph showing the rate of a change in the content of a stabilizing oxide in a solid electrolyte layer in an oxygen sensing element according to the invention kept in a high temperature atmosphere and the same matter in another oxygen sensing element which is not in accordance with the invention.

In the experiment, the samples of the two kinds of oxygen sensing elements were kept in an electric furnace in which the temperature of air was maintained constantly at 600° C., and the content (mole %) of $Y_2O_3$ in the solid electrolyte layer 22 of every sample was measured by X-ray diffraction analysis at intervals of 50 hr. The results of this experiment are shown in FIG. 4, wherein the curve A represents the oxygen sensing element 10 according to the invention and the curve B represents the oxygen sensing element produced by omitting the barrier layer. The remarkable effect of the barrier layer 16 on the electrical characteristics of the oxygen sensing element 10 according to the invention can be understood from a comparison between the curve A and B in FIG. 4.

As a supplementary experiment, the output characteristics of the samples of the two kinds of oxygen sensing elements subjected to the above described 600° C. aging test were measured in the following way. Each sample was disposed in an experimental gas atmosphere in which the partial pressure of oxygen was varied over the range of $10^2$ to $10^{-4}$ Pa, and a constant DC current of 50 μA was made to flow from the first elecrode layer 18 to the second electrode layer 20 through the solid electrolyte 22 existing between the two electrode layers, while the heater 14 was energized so as to maintain the oxygen sensing element constantly at 600° C.

Figure 5:
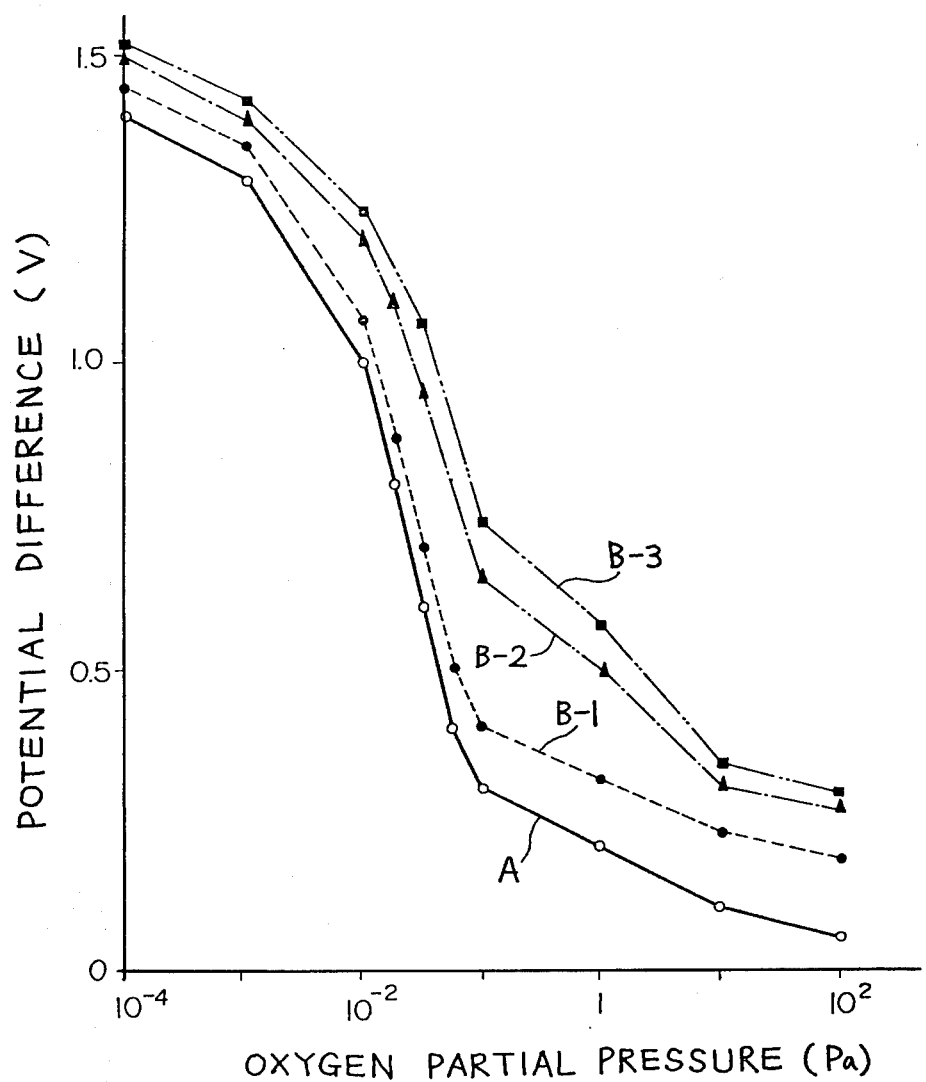
FIG. 5 is a graph showing the effect of long heating on the output characteristic of an oxygen sensing element according to the invention and another oxygen sensing element which is not in accordance with the invention.

FIG. 5 shows the results of this experiment. Before the above described aging test, the relationship between the partial pressure of oxygen in the gas atmosphere and the output voltage, i.e. potential difference V according to the hereinbefore presented equation, of the oxygen sensing element 10 according to the invention was as represented by the curve A. The oxygen sensing element produced by omitting the barrier layer exhibited an identical output characteristic (i.e. curve A). In the case of the element 10 according to the invention, the samples subjected to the 600° C. aging test for 100 hr, for 200 hr and for 300 hr exhibited practically no change in the relationship between the partial pressure of oxygen in the gas atmosphere and the potential difference V from the curve A. In the case of the oxygen sensing element not having the barrier layer, the samples subjected to the 600° C. aging test for 100 hr exhibited a different output characteristic as represented by the curve B-1, and the samples subjected to the aging test for 200 hr and for 300 hr exhibited still different output characteristics as represented by the curves B-2 and B-3, respectively. The results of these experiments verify the presumption that a significant decrease in the content of a stabilizing oxide such as $Y_2O_3$ in the solid electrolyte layer 22 by diffusion of the stabilizing oxide out of this layer will cause significant changes in the resistance of the solid electrolyte and the polarizing characteristics at the interfaces between the solid electrolyte and the first and second electrode layers.

Figure 6:
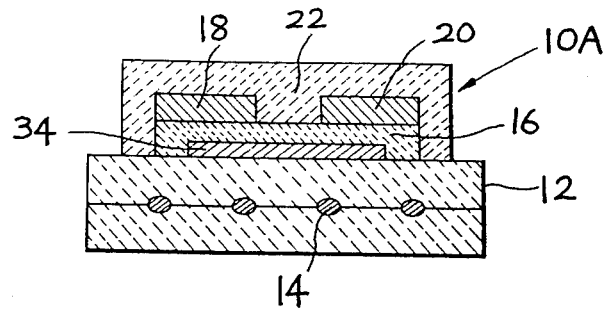
FIG. 6 shows a preferred modification of the oxygen sensing element of FIG. 1 in a similar view.

The curve A in FIG. 4 indicates that the barrier layer 16 in FIG. 1 permits a little diffusion of $Y_2O_3$ out of the solid electrolyte 22 existing between the first and second electrode layers 18 and 20. Therefore, it is preferred to modify the oxygen sensing element of FIG. 1 in the way as shown in FIG. 6. In the modified oxygen sensing element 10A of FIG. 6, there is a supplementary barrier layer 34 which is formed of platinum and directly covers the upper surface of the substrate 12 at least in a region just beneath the lateral gap between the first and second electrode layers 18 and 20, and the $ZrO_2-Y_2O_3$ barrier layer 16 is formed on the supplementary barrier layer 34. The supplementary barrier layer 34 is provided because $Y_2O_3$ or any other stabilizing oxide added to an oxygen ion conductive solid electrolyte hardly diffuses into a metal, and practically never diffuses into platinum. In element 10A the barrier layer 16 formed of a solid electrolyte composition is indispensable because the platinum barrier layer 34 must be isolated from the electrode layers 18 and 20.

Figure 7:
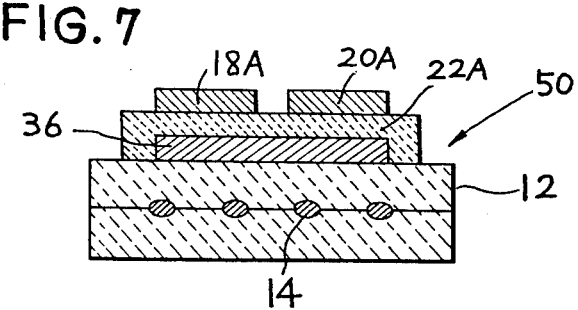
FIG. 7 is a sectional and explanatory view of an oxygen sensing element as another embodiment of the invention.

FIG. 7 shows an oxygen sensing element 50 which is similar in principle to the elements 10 and 10A of FIGS. 1 and 6 but is different in design. In this element 50, the ceramic substrate 12 and the heater 14 are identical with the counterparts in FIG. 1. A barrier layer 36 formed of platinum covers a central region of the upper surface of the substrate 12, and an oxygen ion conductive solid electrolyte layer 22A having a microscopically porous structure is formed on the barrier layer 36. A first electrode layer 18A and a second electrode layer 20A are formed on the outer surface of the solid electrolyte layer 22A in a spaced arrangement such that both the solid electrolyte 22A and the platinum layer 36 exist right beneath the lateral gap between these two electrode layers 18A and 20A. Similarly to the electrode layers 18 and 20 in FIG. 1, the elecrode layers 18A and 20A in FIG. 7 are formed of platinum or its alloy and have a microscopically porous structure. It will be understood that the effect of the barrier layer 36 in this oxygen sensing element 50 is similar to the effect of the barrier layer 34 in FIG. 6.

Figure 8:
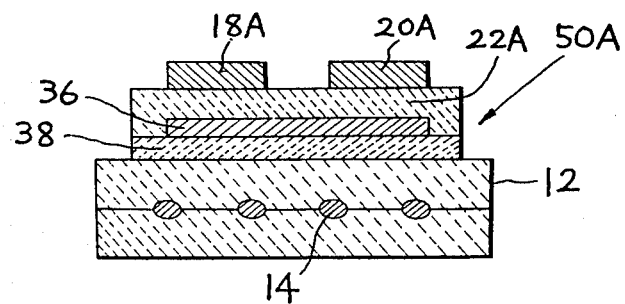
FIG. 8 shows a preferred modification of the oxygen sensing element of FIG. 7 in a similar view.

FIG. 8 shows a preferred modification of the oxygen sensing element 50 of FIG. 7. In the modified element 50A, there is an intermediate layer 38 between the upper surface of the substrate 12 and the barrier layer 36. The intermediate layer 38 is formed of a ceramic material, which is preferably the same solid electrolyte as the material of the overlying layer 22A, and is added with a view to enhancing the strength of adhesion of the laminated sensitive part to the ceramic substrate 12 than in the case of forming the barrier layer 36 of platinum or any other metal directly on the surface of the ceramic substrate 12.

The foregoing description of preferred embodiments of the invention have been presented for purposes of illustration and description. They are not intended to be exhaustive or to limit the invention to the precise forms disclosed, and obviously many modifications and variations are possible in light of the above teachings. The embodiments were chosen and described in order to best explain the principles of the invention and its practical applicaton to thereby enable others skilled in the art to best utilize the invention in various embodiments and with various modifications as are suited to the particular use contemplated. It is intended that the scope of the invention be defined by the claims appended hereto.

What is claimed is:
1. An oxygen sensing element comprising:
a substrate made of a first ceramic material;
a ceramic diffusion barrier layer made of a second ceramic material and formed on a major surface of the substrate;
a microscopically porous layer comprising an oxygen ion conductive solid electrolyte containing a stabilizing oxide formed on the barrier layer; and
microscopically porous reference and measurement electrode layers which are formed on one side of the solid electrolyte layer so as to be spaced from each other,
wherein the diffusion barrier layer, the solid electrolyte layer and the reference and measurement electrode layers are arranged such that the diffusion barrier layer is positioned between the substrate and the solid electrolyte layer, at least in a region between the reference and measurement electrode layers, the diffusion barrier layer comprising an inorganic heat-resistant material operable to limit diffusion of said stabilizing oxide contained in the solid electrolyte to a greater extent than said first ceramic material.

2. An oxygen sensing element according to claim 1, wherein the ceramic diffusion barrier layer comprises said solid electrolyte containing said stabilizing oxide.

3. An oxygen sensing element according to claim 1 or 2, wherein the reference and measurement electrode layers are in close contact with an outer surface of the ceramic diffusion barrier layer, said solid electrolyte layer being arranged to substantially cover outer surfaces of the reference and measurement electrode layers and to make direct contact with the outer surface of the barrier layer in a region between the reference and measurement electrode layers.

4. An oxygen sensing element comprising:
a substrate made of a ceramic material;
a two-layer diffusion barrier structure formed on a major surface of the substrate;
a microscopically porous layer comprising an oxygen ion conductive solid electrolyte containing a stabilizing oxide formed on the barrier layer;
microscopically porous reference and measurement electrode layers formed on one side of the solid electrolyte layer so as to be spaced from each other and in contact with an outer layer of said barrier structure;
said diffusion barrier structure comprising an inner sheet like metallic layer formed directly on said major surface of the substrate, and an outer ceramic layer formed on said inner layer and positioned between said inner layer and said reference and measurement electrode layers;
wherein the diffusion barrier structure, the solid electrolyte layer and the reference and measurement electrode layers are arranged such that the diffusion barrier structure is positioned between the substrate and the solid electrolyte layer, at least in a region between the reference and measurement electrode layers, said two layer diffusion barrier structure comprising inorganic, heat-resistant materials operable to limit diffusion of said stabilizing oxide contained in the solid electrolyte to a greater extent than said first ceramic material.

5. An oxygen sensing element according to claim 4, wherein said inner layer comprises platinum.

6. An oxygen sensing element according to claim 4, wherein said outer layer comprises said solid electrolyte.

* * * * *